United States Patent [19]
Matthews et al.

[11] Patent Number: 5,859,187
[45] Date of Patent: Jan. 12, 1999

[54] ANTIVIRAL PEPTIDES

[75] Inventors: James T. Matthews, Bedminster; Katerina Leftheris, Skillman; Robert K. Hamatake, Lawrenceville, all of N.J.; John T. Stevens, Levittown, Pa.; Mary L. Haffey, Lawrenceville, N.J.

[73] Assignee: E. R. Squibb & Sons, Inc., Princeton, N.J.

[21] Appl. No.: 828,789

[22] Filed: Jan. 29, 1992

Related U.S. Application Data

[63] Continuation-in-part of Ser. No. 332,203, Apr. 3, 1989, Pat. No. 5,120,639.
[51] Int. Cl.$^6$ .......................... A61K 38/00; A61K 38/04; A61K 39/245; A61K 39/25
[52] U.S. Cl. .......................... 530/326; 530/327; 530/328; 530/350; 424/231.1
[58] Field of Search ...................................... 530/324, 325, 530/326, 327, 328; 424/94.1; 514/2

[56] References Cited

PUBLICATIONS

Thomas et al. Joun. of Virology vol. 62(5) pp. 1550–1557 May 1988.

*Primary Examiner*—Lynette F. Smith
*Attorney, Agent, or Firm*—Stephen B. Davis

[57] ABSTRACT

Inhibition of UL42 stimulation of herpesvirus DNA polymerase activity is exhibited by novel compounds of the formulas $$W'-A_1-A_2-A_3-A_4-A_5-A_6-A_7-A_8-A_9-A_{10}-A_{11}-X$$
[SEQ. ID NO: 1]

and $$Y'-A_{12}-A_{13}-A_{14}-A_{15}-A_{16}-A_{17}-Z \text{ [SEQ. ID NO: 2]}$$

that are useful as antiviral agents.

14 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Xaa Xaa Xaa Xaa Xaa Xaa Xaa Xaa Xaa Xaa Xaa Xaa
1               5                   10

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Xaa Xaa Xaa Xaa Xaa Xaa
1               5

( 2 ) INFORMATION FOR SEQ ID NO:3:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:3:

Ala Pro Gly Asp Glu Pro Ala Pro Pro Tyr
 1           5                    10

( 2 ) INFORMATION FOR SEQ ID NO:4:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Ala Pro Gly Asp Glu Pro Ala Pro Pro
 1           5

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Ala Ala Pro Gly Asp Glu Pro Ala Pro Pro
 1           5                    10

( 2 ) INFORMATION FOR SEQ ID NO:6:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Ala Ala Ala Pro Gly Asp Glu Pro Ala Pro Pro
 1           5                    10

( 2 ) INFORMATION FOR SEQ ID NO:7:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Ala Gly Ala Thr Ala Glu Glu Thr Ala Tyr
 1           5                    10

( 2 ) INFORMATION FOR SEQ ID NO:8:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

Ala Gly Ala Thr Ala Glu Glu Thr Ala Ala
 1               5                  10

(2) INFORMATION FOR SEQ ID NO:9:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:9:

Gly Ala Thr Ala Glu Glu Thr Ala
 1               5

(2) INFORMATION FOR SEQ ID NO:10:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:10:

Ala Gly Ala Thr Ala Glu Glu Thr Ala
 1               5

(2) INFORMATION FOR SEQ ID NO:11:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Glu Glu Thr Arg Arg Met Leu His Arg Ala Phe Asp Thr Leu Ala
 1               5                  10                  15

(2) INFORMATION FOR SEQ ID NO:12:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:12:

Ala Pro Gly Asp Glu Pro Ala Pro Pro
 1               5

ANTIVIRAL PEPTIDES

This application is a continuation-in-part of U.S. Ser. No. 332,203 filed Apr. 3, 1989 now U.S. Pat. No. 5,120,639.

BACKGROUND OF THE INVENTION

Herpesvirus are a diverse group of large DNA viruses found in many different animal species, including man. These viruses are known to cause a number of diseases in the hosts they infect. For example, different human herpesviruses are the causative agents of various diseases such as oral [herpes simplex virus type 1 (HSV-1)] and genital [herpes simplex virus type 2 (HSV-2)] herpes simplex, cytomegalic inclusion disease [cytomegalovirus (CMV)] and infectious mononucleosis [Epstein Baar virus (EBV)].

Seven viral-encoded gene products which are essential for HSV DNA replication have been identified. These include the HSV DNA polymerase (UL30) and the accessory protein, UL42. The essential function of UL42 is believed to be by forming a complex with and stimulation of the processivity of the viral polymerase. The region of HSV DNA polymerase which binds UL42 has been genetically mapped to the carboxy-terminal 227 amino acids.

Despite extensive knowledge concerning the characteristics of herpesviruses, and with the increasing incidence of clinical resistance to the currently licensed anti-herpes drugs, new materials and methods are still needed for combatting diseases caused by these viruses.

SUMMARY OF THE INVENTION

The present invention concerns peptides based on the deduced amino acid sequence of the herpes simplex virus (HSV) DNA polymerase which are able to inhibit the UL42 stimulation of the herpes simplex virus DNA polymerase activity and are, therefore, useful as antiviral agents. These peptides correspond to or are derived from certain regions of herpes simplex virus DNA polymerase, that is, amino acid residues 1098 to 1108 and 1216 to 1235 of HSV DNA polymerase.

In particular, the present invention concerns compounds of formula I

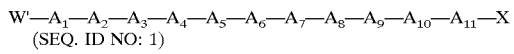
(SEQ. ID NO: 1)

and

(SEQ. ID NO: 2)

that are useful as antiviral agents. In formulas I and II and throughout the specification, W' and Y' are H—, $CH_3$—, or $CH_3CO$—; $A_1$ is $R_1$, $R_1$-$R_2$ or deleted, wherein $R_1$ and $R_2$ are alanine, glycine, valine or leucine; $A_2$ and $A_8$ are alanine, glycine, valine or leucine; $A_3$, $A_7$, $A_9$ and $A_{10}$ are proline or hydroxyproline, $A_4$ is glycine or alanine; $A_5$ is aspartic acid or glutamic acid; $A_6$, $A_{13}$ and $A_{14}$ are glutamic acid or aspartic acid; $A_{11}$ is tyrosine, phenylalanine or deleted; X and Z are —OH, —$NH_2$ or —$NH_2CH_3$; $A_{12}$ is $R_3$—$R_4$— $R_5$—$R_6$—$R_7$, —$R_8$—$R_9$—$R_{10}$—$R_{11}$ or deleted, wherein $R_3$, $R_5$, $R_7$, $R_9$ and $R_{11}$ are alanine, glycine, valine or leucine, $R_4$ and $R_8$ are glycine or alanine, and $R_6$ and $R_{10}$ are threonine or serine; $A_{15}$ is threonine or serine; $A_{16}$ is arginine or lysine; $A_{17}$ is arginine, lysine, tyrosine, phenylalanine, $R_{12}$—$R_{13}$— $R_{14}$— histidine-$R_{15}$—$R_{16}$—$R_{17}$—$R_{18}R_{19}$—$R_{20}$—$R_{21}$ or deleted, wherein $R_{12}$ and $R_{15}$ are arginine or lysine, $R_{13}$ is methionine or norleucine, $R_{14}$ and $R_{20}$ are leucine, norleucine, valine or isoleucine, $R_{16}$ and $R_{21}$ are alanine, glycine, valine or leucine, $R_{17}$ is phenylalanine or tyrosine, $R_{18}$ is aspartic acid or glutamic acid, and $R_{19}$ is threonine or serine. Preferred are compounds wherein W' is H—, $A_1$ is alanine-alanine, $A_2$ is alanine, $A_3$ is proline, $A_4$ is glycine, $A_5$ is aspartic acid, $A_6$ is glutamic acid, $A_7$ is proline, $A_8$ is alanine, $A_9$ is proline, $A_{10}$ is proline, $A_1$ is deleted and X is $NH_2$, and wherein Y' is H, $A_{12}$ is alanine-glycine-alanine-threonine-alanine, $A_{13}$ is glutamic acid, $A_{14}$ is glutamic acid, $A_{15}$ is threonine, $A_{16}$ is arginine, $A_{17}$ is tyrosine and Z is $NH_2$.

DETAILED DESCRIPTION OF THE INVENTION

The compounds of formula I and formula II and the pharmaceutically acceptable salts thereof, are antiviral agents that can be used to treat viral infections in mammalian species such as domesticated animals (eg., dogs, cats, horses, cattle and the like) and humans, as well as in avian species (eg., chickens and turkeys). The compounds of formula I and formula II are effective against one or both of the following viruses: herpes simplex virus types 1 and 2. They are also believed to be active against a variety of other DNA viruses. Exemplary DNA viruses in addition to those named include other herpes viruses (eg., cytomegalovirus, Epstein-Barr virus, human herpes virus 6, pseudorabies virus, varicella zoster virus and the like).

The compounds of this invention may be administered parenterally (for example, by intravenous, intraperitoneal or intramuscular injection), or topically. The compounds may be administered parenterally in an amount effective to treat the infection. The dosage will depend on the severity of infection, but will likely be in the range of 0.1 to 100 mg/kg body weight. The desired dose may be administered several times daily at appropriate intervals.

For infections of the eye, or other external tissues (eg., mouth and skin), the composition may be applied to the infected part of the body of the patient topically as an ointment, cream, aerosol, gel, powder, lotion, suspension or solution (eg., as eye drops). The concentration of the compound in the vehicle will depend on the severity of the infection, but will likely be in the range from 0.1 to 7% by weight.

The compounds of formula I and formula II can be formulated in compositions such as sterile solutions or suspensions for parenteral administration. About 1 to 500 milligrams of a compound of formula I or formula II is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

Although no particular mechanism of action is asserted, it is believed that the mechanism by which the peptides of the present invention work as antiviral agents is by binding to the accessory protein UL42, preventing the productive association of UL42 and herpes simplex virus DNA polymerase. The result is an inhibition of the stimulation of HSV DNA polymerase activity by UL42. These compounds do not appear to inhibit the intrinsic polymerizing activity of the HSV DNA polymerase.

The compounds of the present invention can also be used to generate neutralizing antisera which specifically inhibit the activity of HSV DNA polymerase, as described in copending U.S. patent application Ser. No. 332,203 filed Apr. 3, 1989. This application is incorporated herein by reference. As discussed in this patent application, two peptides, having the amino acid sequences Ala-Pro-Gly-Asp-Glu-Pro-Ala-Pro-Pro-Tyr (SEQ. ID NO: 3) and Ala-Gly-Ala-Thr-Ala-Glu-Glu-Thr-Arg-Tyr [SEQ. ID NO: 7], can be used to raise antibodies which specifically neutralize HSV-1 and HSV-2 DNA polymerase. These peptides correspond to two carboxy terminal peptides (HSV-1 residues 1100–1108 and 1216–1224, respectively). For both peptides, the C-terminal tyrosine was added to facilitate coupling to bovine serum albumin (BSA) and thyroglobulin. However, any suitable amino acid residue such as cysteine can be used to facilitate coupling. Any suitable amino acid can be substituted provided the antibody generated has the same function as the antibody generated against the parent peptide.

The compounds of the present invention wherein C-termini of the peptides are terminated with a carboxy group may be prepared by the following general approach, as illustrated for the compound of formula I wherein $A_{10}$ is proline, $A_{11}$ is deleted and X is —OH. This preparation may be carried out on an automated peptide synthesizer (e.g., Biosearch 9600) using standard software protocols.

A compound of the formula III

Apro-Pro'-O-PAM RESIN wherein Apro is an amino-protecting group (e.g., t-butoxycarbonyl) attached at the amino terminus, and Pro' is proline or an amino acid residue derived therefrom having a sidechain-protecting group, are used as starting materials. The compound of formula III is treated with, in sequence:

(a) a deprotecting agent (e.g., trifluoroacetic acid) in an inert solvent (e.g., methylene chloride) in the presence of one or more cation scavengers (e.g., dimethylphosphate, anisole);

(b) a tertiary base (e.g., diisopropylethylamine); and (c) an amino acid of the formula IV Apro-Pro'-OH (wherein Pro' is proline or an amino acid residue derived therefrom having a sidechain-protecting group) in an inert solvent (e.g., dimethylformamide) in the presence of a coupling reagent (e.g., diisopropyl-carbodiimide) in an inert solvent (e.g., methylene chloride); to form the compound of the formula V Apro-Pro'-Pro'-O-PAM-RESIN Presence of an agent which suppresses racemization or dehydration (e.g., hydroxybenzotriazole) is optional. Step (c) above may be followed by treatment with an amino acid acetylating agent (e.g., acetylimidazole) which acetylates or "caps" unreacted amino acids. This method can also be used to acetylate the N-terminus of the side-chain protected resin bound product.

The foregoing process is repeated with the resin-linked amino acid chain until the N-terminal amino acid residue has been coupled to the polypeptide. One may also use multiple peptide synthesis techniques, which are generally known in the art. See, e.g., Tjoeng et al., "Multiple Peptide Synthesis Using a Single Support (MPS3)" *Int. J. Protein Peptide Res.* 35, 141–146 (1990).

As noted above, sidechain-protecting groups may be used in this process for sidechains having reactive functionalities, such as hydroxyl, carboxyl, amino, mercapto, guanidino, imidazolyl, indolyl and the like. The particular protecting groups used for any particular amino acid residue depends upon the sidechains to be protected and are generally known in the art. Exemplary sidechain-protecting groups are benzyl, halocarbobenzoxy, and the like for hydroxyl; cyclohexyl, benzyl and the like for carboxyl; 4-methylbenzyl, acetamidomethyl and the like for mercapto; carbobenzoxy, halocarbobenzoxy and the like for amino; 2,4-dinitrophenyl, benzyloxymethyl and the like for indolyl; and tosyl, nitro and the like for guanidino.

Sidechain-protecting groups may be removed, if desired, by treatment with one or more deprotecting agents in an inert solvent or solvent mixture (e.g., dimethylformamide, methylene chloride). Suitable deprotecting agents are generally known in the art. Exemplary deprotecting agents are thiophenol, mercaptoethanol and the like for removing 2,4-dinitrophenyl; trifluroacetic acid and the like for butoxycarbonyl; hydrofluoric acid, trifluoromethanesulfonic acid and the like for several different protecting groups.

In the situation where it is desired to prepare compounds of the present invention wherein the C-terminus of the peptides is terminated with a primary amine group, the resin —NH—MBHA, wherein MBHA is a methyl benzhydryl linker coupled to a polystyrene-divinyl resin, may be substituted for the —O-PAM-RESIN in the above protocol.

In the situation where it is desired to prepare peptides of the present invention containing C-terminal N-methyl amides, the peptides may be assembled on a brominated PPOA resin [See, D. Ellof and M. Mutter, Chimia 39, 10 (1985)]. Treatment of the protected peptide resin with N-methylamine/dioxane cleaves the protected peptide from the resin. The sidechain protecting groups can then be removed by conventional deprotection methods well established in the art as described above.

The following examples are further illustrative of the present invent. These examples are not intended to limit the scope of the present invention and provide further understanding of the invention.

EXAMPLE 1

The compounds of the present invention can be prepared, and the compounds described in Examples 2 and 3 herein below were prepared, using the following general procedure.

The compounds were synthesized by solid phase techniques on an Applied Biosystems Model 430A Peptide Synthesizer using Boc/HOBt/NMP (tert-butoxycarboxyl/hydroxybenzotriazole/N-methyl-pyrdidone) chemistry. Procedure A (as outlined in the Applied Biosystems manual) was used for the chemical synthesis of peptides derived from HSV-1 DNA polymerase. Preparation began with a resin containing the nitrogen-protected amino acid which was sidechain protected if reactive (0.5 mmoles). The remaining protected amino acids were assembled on the peptide-resin according to the detailed procedure A outlined below;

Procedure A

1. The resin was washed once with dichloromethane (DCM).

2. The resin was treated for 30 minutes with 30% TFA (trifluoroacetic acid)/DCM.

3. The resin was treated for 17 minutes with 50% TFA/DCM.

4. The resin was washed 5 times with DCM.

5. The resin was washed with 5% diisopropylethylamine (DIEA) in DCM for 1 minute.

6. The resin was washed with 5% DIEA in N-methylpyrolidone (NMP) for 1 minute.

7. The resin was washed 5 times with NMP.

8. The suitably protected Boc-amino acid was coupled to the α amine of the resin-bound peptide using the following protocol;
   a. The suitably protected amino acid (2 mmoles) was dissolved in 3.25 mL of NMP containing 2 mmoles of hydroxybenzotriazole (HOBt).
   b. To this was added 2 mL of NMP containing 2 mmoles of dicyclohexylcarbodiimide (DCC). This mixture was allowed to stand with intermittant vortexing for 36–46 minutes.
   c. The dicyclohexylurea (DCU) was filtered off and the solution was added to the peptide-resin at which time the coupling was allowed to proceed for 30 minutes.
   d. DMSO (dimethyl sulfoxide) was added to provide 20% DMSO coupling solution for 16 minutes.
   e. 3.8 equivalents of DIEA was added to the coupling solution for 7 minutes.

9. The resin was washed 3 times with DCM.

10. A capping solution of 10% Ac$_2$O (acetic anhydride) and 5% DIEA in DCM was added to the resin and the mixture was vortexed for 2 minutes followed by draining.

11. A capping solution of 10% Ac$_2$O in DCM was added to the resin and the mixture was vortexed for 2 minutes followed by draining.

12. The peptide resin was washed 4 times with DCM.

13. Steps 1–12 were repeated for each protected amino acid to be coupled.

14. The resin was treated for 30 minutes with 30% TFA/DCM.

15. The resin was treated for 17 minutes with 50% TFA/DCM.

16. The resin was washed 5 times with DCM, and dried under nitrogen.

EXAMPLE 2

L-Alanyl-L-glycyl-L-alanyl-L-threonyl-L-alanyl-L-glutamyl-L-glutamyl-L-threonyl-L-arginyl-L-arginine For the preparation of H-Ala-Gly-Ala-Thr-Ala-Glu-Glu-Thr-Arg-Arg-OH (SEQ. ID NO: 8), tBoc-Arg(Mts)-PAM resin (phenylacetamidomethyl linker coupled to polystyrene crosslinked with 1% divinylbenzene), 0.61 meq/g, 0.74 g, 0.45 mmol, Applied Biosystems) was subjected to Procedure A, as described above in Example 1. Amino acids were coupled as their Nα t-Boc derivatives (2 mmol). The sidechain carboxyl group of Glu was protected as the benzyl ester while the sidechain hydroxyl group of Thr was protected as the benzyl ether and the sidechain guanidino group of Arg was protected as the mesitylenesulfonamide (Mts).

The peptide was simultaneously deprotected and cleaved from the resin by treatment with anhydrous liquid HF as follows: 1 g (0.324 mmol) of the protected peptide resin (the N-terminal Boc group had been previously removed as described above in Example 1) was placed into a Kel-F HF reaction vessel with a stir bar. The following scavengers were added; 1 mL anisole, 1 mL dimethylsulfide and 3 mg mercaptopyridine. The vessel was evacuated in the HF apparatus and cooled in a dry ice/isopropanol bath. Approximately 10 mL of HF was distilled from a cylinder into the reaction vessel, and the dry ice bath was replaced with an ice water bath. The reaction was stirred at −5° C. for 1.5 hours, followed by HF removal under vacuum for 20 minutes. The product was precipitated and washed with ether, then dissolved in 30% aqueous acetic acid and separated from the resin by filtration. The filtrate was frozen on dry ice and lyophilized to give the crude peptide product. The peptide was dissolved in water and passed through 30 g (8×23 cm column) of prepared Biorad AGlx2 anion exchange resin in the acetate form. The collected fractions were tested using the quantitative ninhydrin test. Those fractions giving a positive reading (blue color) were pooled and lyophilized to give the crude peptide product in the acetate form. The peptide was dissolved in water, membrane-filtered and sample aliquots were applied to a Prep HPLC column (C$_{18}$, 20×250 mm, 5 p, 120 A). Fractions containing product were collected and analysed by analytical RP-HPLC. Fractions containing product with a minimum purity of 98% were pooled and lyophilized to afford the product (29%) as a white, fluffy powder.

MS (M+H)$^+$1061, sequence analysis and amino acid analysis were correct for this peptide.

EXAMPLE 3

L-Alanyl-L-prolyl-L-glycyl-L-aspartyl-L-glutamyl-L-prolyl-L-alanyl-L-prolyl-L-proline For the preparation of H-Ala-Pro-Gly-Asp-Glu-Pro-Ala-Pro-Pro-OH (SEQ. ID NO: 12), tBoc-Pro-PAM resin (phenylacetamidomethyl linker coupled to polystyrene crosslinked with 1% divinylbenzene, 0.19 meq/g, 1.32 g, 0.25 mmol, Advanced Chemtech) was subjected to Procedure A as described above in Example 1. Amino acids were coupled as their Nα t-Boc derivatives (2 mmol). The sidechain caroxyl group of Glu was protected as the benzyl ester and the sidechain carboxyl group of Asp was protected as the cyclohexyl ester.

The peptide was simultaneously deprotected and cleaved from the resin by treatment with anhydrous liquid HF as follows: 1 g of peptide resin was placed into the Kel-F HF reaction vessel with a stir bar. The following scavengers were added; 1 mL anisole, 1 mL dimethylsulfide and 3 mg mercaptopyridine. The vessel was evacuated in the HF apparatus and cooled in a dry ice/isopropanol bath. Approximately 10 mL HF was distilled from a cylinder into the reaction vessel, and the dry ice bath was replaced with an ice cylinder into the reaction vessel, and the dry ice bath was replaced with an ice water bath. The reaction was stirred at −5° C. for 1 hour, followed by HF removal under vacuum for 20 minutes. The product was precipitated and washed with ether, then dissolved in 30% aqueous acetic acid and separated from the resin by filtration. The filtrate was frozen on dry ice and lyophilized to yield crude peptide product. The peptide was passed through 30 g (8×23 cm column) of prepared Biorad AGlx2 anion exchange resin in the acetate form. The collected fractions were tested using the quantitative ninhydrin test. Those fractions giving a positive reading (blue color) were pooled and lyophilized. The peptide was dissolved in 20% HOAc, membrane-filtered and sample aliquots were applied to a Prep HPLC column (C$_{18}$, 20×250 mm, 5μ, 120 A). Fractions were collected and analysed by analytical RP-HPLC. Those containing the desired peptide with a minimum purity of 98% were pooled and lyophilized to afford the product (24%) as a white, fluffy powder.

MS (M+H)$^+$850.1, sequence analysis and amino acid analysis were correct for this peptide.

EXAMPLE 4

L-Alanyl-L-prolyl-L-glycyl-L-aspartyl-L-glutamyl-L-prolyl-L-alanyl-L-prolyl-L-prolyl-L-tyrosineamide; and L-Alanyl-L-glycyl-L-alanyl-L-threonyl-L-alanyl-L-glutamyl-L-glutamyl-L-threonyl-L-arginyl-L-tyrosineamide The peptides of the formulas H-Ala-Pro-Gly-Asp-Glu-Pro-Ala-Pro-Pro-Tyr-$NH_2$ (SEQ. ID NO: 3) and H-Ala-Gly-Ala-Thr-Ala-Glu-Glu-Thr-Arg-Tyr-$NH_2$ (SEQ. ID NO: 7) were synthesized suing Boc or F-moc protected amino acids. The resin used was polystyrease +a linker. The peptides were purified by HPLC on a VyDac C-18 column using as solvent A 0.05% TFA/water and as solvent B 0.05% TFA/acetonitrile, a gradient consisting of 5% solvent B for 3 minutes followed a 20 minute gradient from 5–100% solvent B was used. Peptides were quantitated by integration in comparison to a known standard. Peptide purity and integrity was assayed by FAB-MS.

EXAMPLE 5

L-Alanyl-L-prolyl-L-glycyl-L-aspartyl-L-glutamyl-L-prolyl-L-alanyl-L-prolyl-L-prolineamide; L-Alanyl-L-alanyl-L-prolyl-L-glycyl-L-aspartyl-L-glutamyl-L-prolyl-L-alanyl-L-prolyl-L-prolineamide; L-Alanyl-L-alanyl-L-alanyl-L-prolyl-L-glycyl-L-aspartyl-L-glutamyl-L-prolyl-L-alanyl-L-prolyl-L-prolineamide; L-glycyl-L-alanyl-L-threonyl-L-alanyl-L-glutamyl-L-glutamyl-L-threonyl-L-arginineamide; L-alanyl-L-glycyl-L-alanyl-L-threonyl-L-alanyl-L-glutamyl-L-glutamyl-L-threonyl-L-arginineamide; and L-glutamyl-L-glutamyl-L-threonyl-L-arginyl-L-arginyl-L-methionyl-L-leucyl-L-histidyl-L-arginyl-L-alanyl-L-phenylalanyl-L-aspartyl-L-threonyl-L-leucyl-L-alanine The peptides having the formulas H-Ala-Pro-Gly-Asp-Glu-Pro-Ala-Pro-Pro-$NH_2$ (SEQ. ID NO: 4), H-Ala-Ala-Pro-Gly-Asp-Glu-Pro-Ala-Pro-Pro-$NH_2$ (SEQ. ID NO: 5), H-Ala-Ala-Ala-Pro-Gly-Asp-Glu-Pro-Ala-Pro-Pro-$NH_2$ (SEQ. ID NO: 6), H-Gly-Ala-Thr-Ala-Glu-Glu-Thr-Arg—$NH_2$ (SEQ. ID NO: 9), and H-Ala-Gly-Ala-Thr-Ala-Glu-Glu-Thr-Arg—$NH_2$ (SEQ. ID NO: 10) were prepared using Boc-protected amino acids and benzhydylamine [BHA] resin, while H-Glu-Glu-Thr-Arg-Arg-Met-Leu-His-Arg-Ala-Phe-Asp-Thr-Leu-Ala-OH (SEQ. ID NO: 11) was prepared using Boc-protected amino acids and WANG resin. All of these peptides were purified using a VyDac C-18 column using as solvent A 0.05M Na $H_2PO_4$ and as solvent B 60% acetonitrile in 0.05M $NaH_2PO_4$. A flow rate of 1.0 ml/minute and a linear gradient of 0–100% B over 40 minutes was used.

EXAMPLE 6

I. MATERIALS AND METHODS

A. Cells and Viruses

The culture of *Spodoptera frugiperda* (Sf9) cells and the propagation of the wild type *Autographa californica* nuclear polyhedrosis virus (AcMNPV) and recombinant virus were performed as described in Summers M. D. and Smith, G. E., Texas Agricultural Experimental Station Bulletin 1555 (1987).

B. Construction of Baculovirus Recombinants

The recombinant expressing HSV DNA polymerase (AcMNPV/UL30) has been described previously [Hernandez, J. R. and Lehman, I. R., J. Biol. Chem. 265, (11227–11232 (1990)] and was obtained from Dr. I. R. Lehman (Stanford University).

The recombinant expressing HSV UL42 was prepared as follows. Plasmid pNN4 containing the UL42 gene was obtained from Dr. M. Challberg. (See, Wu, C. A. et al. J. Virol. 62, 435–443 (1988). In order to eliminate an MluI site within UL42 at position 1363 (the A of the start codon is position 1), an intermediate plasmid with a BssHII fragment deleted-designated pUL42del1-was isolated by digestion of pNN4 with BssHII, ligation of the digestion mixture using $T_4$ ligase, and transformation of competent *E. coli* (strain DH5α, Bethesda Research Lab, Gaithersburg, Md.) as suggested by the manufacturer. pUL42del1 was digested with BamHI and MluI, the digestion mixture electrophoresed in an agarose gel and the large DNA fragment isolated using GeneClean.

Two complementary oligomers were synthesized corresponding from the translation start site of UL42 (position 1) to an MluI site within UL42 at position 46 with the sequence GATCCAAAAA preceding the translation start site. Annealing of the oligomers results in a DNA fragment with a 5'-end compatible with BamHI digested DNA and with a 3'-end compatible with MluI digested DNA. The annealed oligomers were ligated to the BamHI-MluI fragment of pUL42del1 to make plasmid pRH103. The intact UL42 gene was reconstructed in the baculovirus expression plasmid by ligation of the BamHI-NdeI fragment from pRH103, the NdeI-NsiI fragment from pNN4, and the BamHI-PstI fragment of pVL1393 [ See, Webb, N. R. and Summers, M. D. Technique 2, 173–188 (1990)]. Plasmid pRH107 resulting from transformation of *E. coli* with the ligation mixture, contains the UL42 gene behind the baculovirus polyhedrin promoter. The production and isolation of the recombinant UL42 baculovirus was performed using standard techniques (Summers and Smith, supra).

C. Purification of HSV UL42 and HSV DNA Polymerase

Sf9 insect cells were grown in suspension culture using Ex-Cell 400 media to 1.5×10⁶ cells/ml at 24° C. and infected at an m.o.i. of 5 with either AcNPV/UL42 or AcNPV/UL30 recombinant baculovirus. After 4 days, the infected cells were harvested and the nuclear fraction isolated as described in Hernandez and Lehman, supra. UL42 protein was purified by sequential chromatography of the nuclear extract on Q-Sepharose, Blue-Sepharose, Phenyl-Superose, Mono S and Superose 12 columns. Individual column fractions were assayed by SDS-PAGE analysis and the identity of the purified protein verified by Western blots using an anti-peptide antibody generated against the N-terminus of UL42 and by the ability to stimulate purified UL30 protein.

Similarly, extracts from the nuclei of a suspension of AcMNPV/polymerase infected Sf9 cells were resolved sequentially by chromatography on phosphocellulose, Phenyl-sepharose, gel filtration and Mono S columns. Individual fractions were assayed for high salt HSV specific DNA polymerase activity as described below. The final purity of the HSV DNA polymerase was 90% as estimated by silver staining of protein gels and appears to contain a doublet of approximately 135 kDa.

D. Measurement of HSV DNA Polymerase Activity

Reactions typically consisted of protein extracts (0.25–5.0 ug), 50 mM Tris-HCl (pH 8.0), 5 mM MgCl 100 mM ammonium sulfate, 1 mM DTT, 5 uM (each) DATP, dCTP, dGTP and [³H]-TTP (540 cpm/pmol), 30 μg of nicked calf thymus DNA per ml, 100 μg of bovine serum albumin per ml in a final volume of 50 μl. All DNA polymerase assays were conducted in duplicate in glass tubes and incubated at 37° C. for 30 minutes. Incorporation into TCA precipitable counts was as described previously [Haffey, M. L., Stevens, J. S., Terry, B. J., Dorsky, D. I., Crumpacker, C. S., Weitstock, S. M., Ruyechon, W. T., and Field, A. K., J. Virol. 62, 4493–4498 (1988)]. Alternately, a second template [10:1 ratio of poly d(A): oligo(T)] was utilized to increase the level of incorporation.

E. Measurement of Polymerase Stimulation by UL42 and Its Inhibition by Peptides

For stimulation studies, the reactions described above contained HSV DNA polymerase (250 ng) together with UL42 (500 ng). For inhibition studies, HPLC purified peptides were pre-incubated with the UL42 and polymerase (30 minutes at 4° C.) prior to the additional of the reaction cocktail.

II. RESULTS

Using the methodology discussed above, the ability of various peptides to inhibit the stimulation by UL42 of the HSV DNA polymerase was studied. In separate specificity assays, the ability of the peptides to inhibit the polymerizing activity of HSV pol in the absence of UL42, the T4 and Klenow polymerase was examined. No inhibitory effect was observed on this polymerization activity. The results of the inhibition by various peptides of stimulation by UL42 of HSV DNA polymerase are summarized in Table I.

TABLE I

Inhibition by Various Peptides of Stimulation by UL42 of HSV DNA Polymerase

| Peptide | IC$_{50}$* |
|---|---|
| H-Ala-Pro-Gly-Asp-Glu-Pro-Ala-Pro-Pro-Tyr-NH$_2$ [SEQ. ID NO: 3] | 161 μM |
| H-Ala-Pro-Gly-Asp-Glu-Pro-Ala-Pro-Pro-NH$_2$ [SEQ. ID NO: 4] | 188 μM |
| H-Ala-Ala-Pro-Gly-Asp-Glu-Pro-Ala-Pro-Pro-NH$_2$ [SEQ. ID NO: 5] | 152 μM |
| H-Ala-Ala-Ala-Pro-Gly-Asp-Glu-Pro-Ala-Pro-Pro-NH$_2$ [SEQ. ID NO: 6] | 90 μM |
| H-Ala-Gly-Ala-Thr-Ala-Glu-Glu-Thr-Arg-Tyr-NH$_2$ [SEQ. ID NO: 7] | 37.5 μM |
| H-Ala-Gly-Ala-Thr-Ala-Glu-Glu-Thr-Arg-Arg-OH [SEQ. ID NO: 8] | 56.6 μM |
| H-Gly-Ala-Thr-Ala-Glu-Glu-Thr-Arg-NH$_2$ [SEQ. ID NO: 9] | 240 μM |
| H-Ala-Gly-Ala-Thr-Ala-Glu-Glu-Thr-Arg-NH$_2$ [SEQ. ID NO: 10] | 88.5 μM |
| H-Glu-Gly-Thr-Arg-Arg-Met-Leu-His-Arg-Ala-Phe-Asp-Thr-Leu-Ala-OH [SEQ. ID NO: 11] | 32.5 μM |
| H-Ala-Pro-Gly-Asp-Glu-Pro-Ala-Pro-Pro-OH [SEQ. ID NO: 12] | 115 μM |

*IC$_{50}$ = Concentration of peptide needed for 50% inhibition of UL42 + HSV DNA polymerase activity.

What is claimed is:

1. A compound having the formula

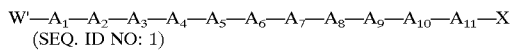
(SEQ. ID NO: 1)

wherein W' is H—, CH$_3$—, or CH$_3$CO—; A$_1$ is R$_1$, R$_1$–R$_2$ or a single bond, wherein R$_1$ and R$_2$ are alanine; A$_2$ and A$_8$ are alanine; A$_3$, A$_7$, A$_9$, and A$_{10}$ are proline; A$_4$ is glycine; A$_5$ is aspartic acid; A$_6$ is glutamic acid; A$_{11}$ is tyrosine or a single bond; X is —OH, —NH$_2$, or —NHCH$_3$.

2. The compound according to claim 1 having the formula H-Ala-Pro-Gly-Asp-Glu-Pro-Ala-Pro-Pro-Tyr-NH$_2$ (SEQ. ID NO: 3).

3. The compound according to claim 1 having the formula H-Ala-Pro-Gly-Asp-Glu-Pro-Ala-Pro-Pro-NH$_2$ (SEQ. ID NO: 4).

4. The compound according to claim 1 having the formula H-Ala-Ala-Pro-Gly-Asp-Glu-Pro-Ala-Pro-Pro-NH$_2$ (SEQ. ID NO: 5).

5. The compound according to claim 1 having the formula H-Ala-Ala-Ala-Pro-Gly-Asp-Glu-Pro-Ala-Pro-Pro-NH$_2$ (SEQ. ID NO: 6).

6. The compound according to claim 1 having the formula H-Ala-Pro-Gly-Asp-Glu-Pro-Ala-Pro-Pro-OH (SEQ. ID NO: 12).

7. A compound having the formula

 (SEQ. ID NO: 2)

wherein Y' is H—, CH$_3$— or CH$_3$CO—, A$_{12}$ is glycine-alanine-threonine-alanine or alanine-glycine-alanine-threonine-alanine; A$_{13}$ and A$_{14}$ are glutamic acid; A$_{15}$ is threonine; A$_{16}$ is arginine; A$_{17}$ is arginine or a single bond; and Z is —OH, —NH$_2$, or —NHCH$_3$.

8. The compound according to claim 7 having the formula H-Ala-Gly-Ala-Thr-Ala-Glu-Glu-Thr-Arg-Tyr-NH$_2$ (SEQ. ID NO: 7).

9. The compound according to claim 7 having the formula H-Ala-Gly-Ala-Thr-Ala-Glu-Glu-Thr-Arg-Arg-OH (SEQ. ID NO: 8).

10. The compound having the formula H-Glu-Glu-Thr-Arg-Arg-Met-Leu-His-Arg-Ala-Phe-Asp-Thr-Leu-Ala-OH (SEQ. ID NO: 11).

11. The compound according to claim 7 having the formula H-Gly-Ala-Thr-Ala-Glu-Glu-Thr-Arg-NH$_2$ (SEQ. ID NO: 9).

12. The compound according to claim 7 having the formula H-Ala-Gly-Ala-Thr-Ala-Glu-Glu-Thr-Arg-NH2 (SEQ. ID NO: 10).

13. A pharmaceutical composition comprising a therapeutically effective amount of the compound according to claim 12 and a pharmaceutically acceptable carrier.

14. A method of treating viral infections comprising administering to a patient in need of such treatment a therapeutically effective amount of a compound according to claim 12.

* * * * *